United States Patent [19]

Guinn et al.

[11] Patent Number: 4,889,812

[45] Date of Patent: Dec. 26, 1989

[54] BIOREACTOR APPARATUS

[75] Inventors: Perry W. Guinn, Oregon City; Gary N. Mills, Gladstone; Robert A. Bedient; Martin O. Greeley, both of Portland, all of Oreg.

[73] Assignee: C. D. Medical, Inc., Miami Lakes, Fla.

[21] Appl. No.: 862,014

[22] Filed: May 12, 1986

[51] Int. Cl.$^4$ .................. C12M 1/04; C12M 1/14; C12M 1/34
[52] U.S. Cl. .................. 435/289; 435/285.311; 435/313; 435/813
[58] Field of Search .............. 435/240.2, 240.21, 244, 435/287, 289, 311, 313, 803, 811, 820, 813, 284, 285

[56] References Cited

U.S. PATENT DOCUMENTS

| | | | |
|---|---|---|---|
| 3,419,473 | 12/1968 | Dawson | 435/240.2 |
| 3,647,633 | 3/1972 | Dawson | 435/240.2 |
| 3,711,372 | 1/1973 | Donnelly | 435/803 |
| 3,732,149 | 5/1973 | Santero | 435/289 |
| 3,806,423 | 4/1974 | Karrenbauer et al. | 435/289 |
| 3,821,087 | 6/1974 | Knazek et al. | |
| 3,893,843 | 7/1975 | Fry et al. | 422/30 |
| 3,911,140 | 10/1975 | Osborne et al. | 435/813 |
| 4,087,327 | 5/1978 | Feder et al. | |
| 4,220,725 | 9/1980 | Knazek et al. | 435/240.242 |
| 4,266,026 | 5/1981 | Breslau | |
| 4,288,228 | 9/1981 | Oberhardt | 422/69 |
| 4,335,215 | 6/1982 | Tolbert et al. | |
| 4,420,398 | 12/1983 | Castino | |
| 4,440,813 | 4/1984 | Michaels et al. | |
| 4,442,206 | 4/1984 | Michaels et al. | 435/813 |
| 4,559,299 | 12/1985 | Rotman | 435/240.2 |
| 4,668,476 | 5/1987 | Bridgham et al. | 435/289 |
| 4,749,654 | 6/1988 | Karrer et al. | 435/240.21 |

FOREIGN PATENT DOCUMENTS

WO86/02378 4/1986 World Int. Prop. O.
WO86/02379 4/1986 World Int. Prop. O.

OTHER PUBLICATIONS

Endotronics brochure "ACUSYST-Jr." 1986, 8500 Evergreen Blvd., Coon Rapids, MN 55433.
Endotronics brochure "ACUSYST-M".
Endotronics brochure "ACUSYST-S".
Amicon brochure, Vitafiber II holow fiber cell culture system.
"VIRTIS Omni-Culture Laboratory Fermenter" brochure, 1984/10M.
Queue Systems brochure, "The New Bioreactor System for Fermentation and Cell Culture", 1986.
Queue Systems brochure, "New Technologies and Products for Cell Culture", 1985.
Queue Systems brochure (untitled) discussing Hybrinet Hollow Fiber Perfusion Bioreactor, 1986.
Queue/Monsanto brochure "Hybrinet Hollow Fiber Bioreactor", 1986.
B. Braun brochure "Biostat M, the Mini-Fermenter for Small Volumes", B05.08.82/1.

(List continued on next page.)

Primary Examiner—Barry S. Richman
Assistant Examiner—Timothy M. McMahon

[57] ABSTRACT

A novel class of bioreactor apparatuses are disclosed which offer improved performance over prior art designs. The apparatuses circulate nutrient fluid through a bioreactor device, such as a hollow fiber bioreactor cartridge, which is used to culture a colony of cells. The nutrient fluid is refreshed by the controlled addition of fresh fluid and the controlled removal of used fluid through a sterile infusion/extraction device. Cellular by-product yield is enhanced by periodically alternating the direction of nutrient fluid through the bioreactor and by periodically circulating the harvest fluid through the extracapillary region of the bioreactor cartridge.

10 Claims, 2 Drawing Sheets

OTHER PUBLICATIONS

L. H. Fermentation, Ltd. brochure "2000 Series Fermenter Range".
Vernay brochure.
Cooney, "Bioreactors: Design and Operation," *Science*, vol. 219, pp. 728–733, 1983.
Tharakan and Chau, "A Radial Flow Hollow Fiber Bioreactor for the Large-Scale Culture of Mammalian Cells," *Biotechnology and Bioengineering*, vol. XVIII, pp. 329–342, 1986.
Feder and Tolbert, "The Large-Scale Cultivation of Mammalian Cells," *Scientific American*, vol. 248, pp. 36–43, Jan. 1983.
Prenosil and Pedersen, "Immobilized Plant Cell Reactors," *Enzyme Microb. Technol.*, vol. 5, pp. 323–331, Sep. 1983.
Park and Kim, "Hollow-Fibre Fermenter Using Ultrafiltration," *Applied Microbiology and Biotechnology*, vol. 22, pp. 190–194, 1985.
Ku, Kuo, et al. "Development of a Hollow-Fiber System for Large-Scale Culture of Mammalian Cells," *Biotechnol. and Bioeng.*, vol. XXIII, pp. 79–95, 1981.

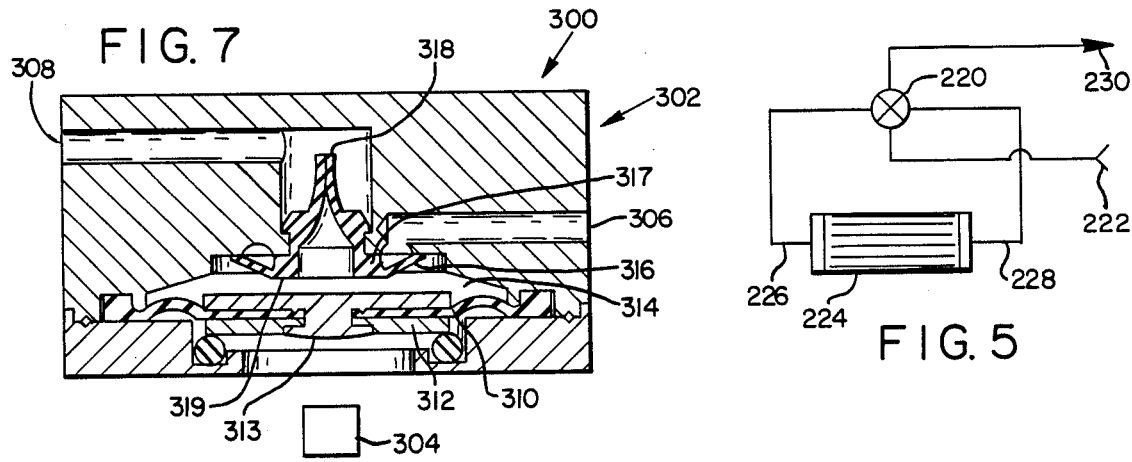
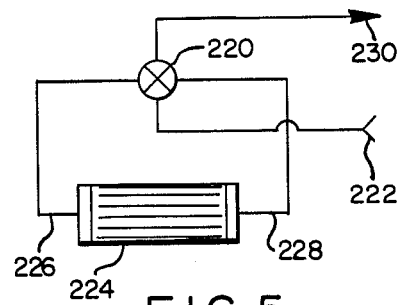
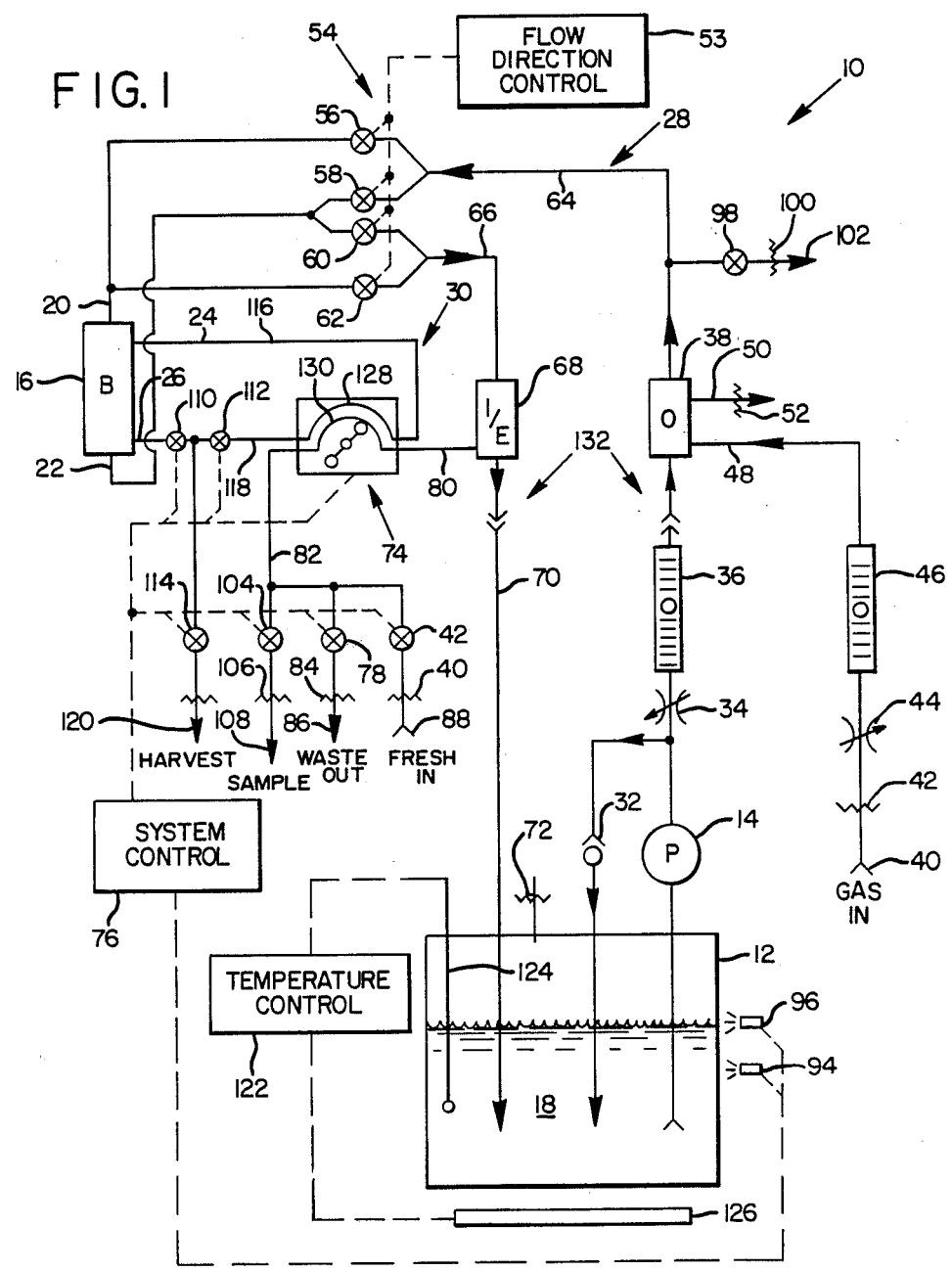

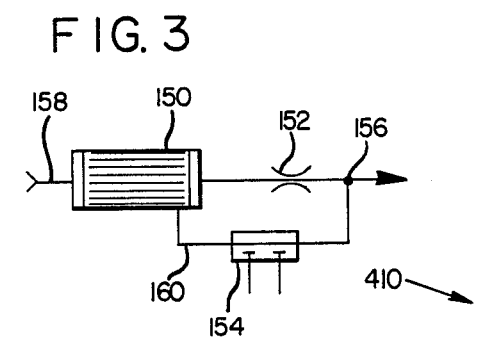
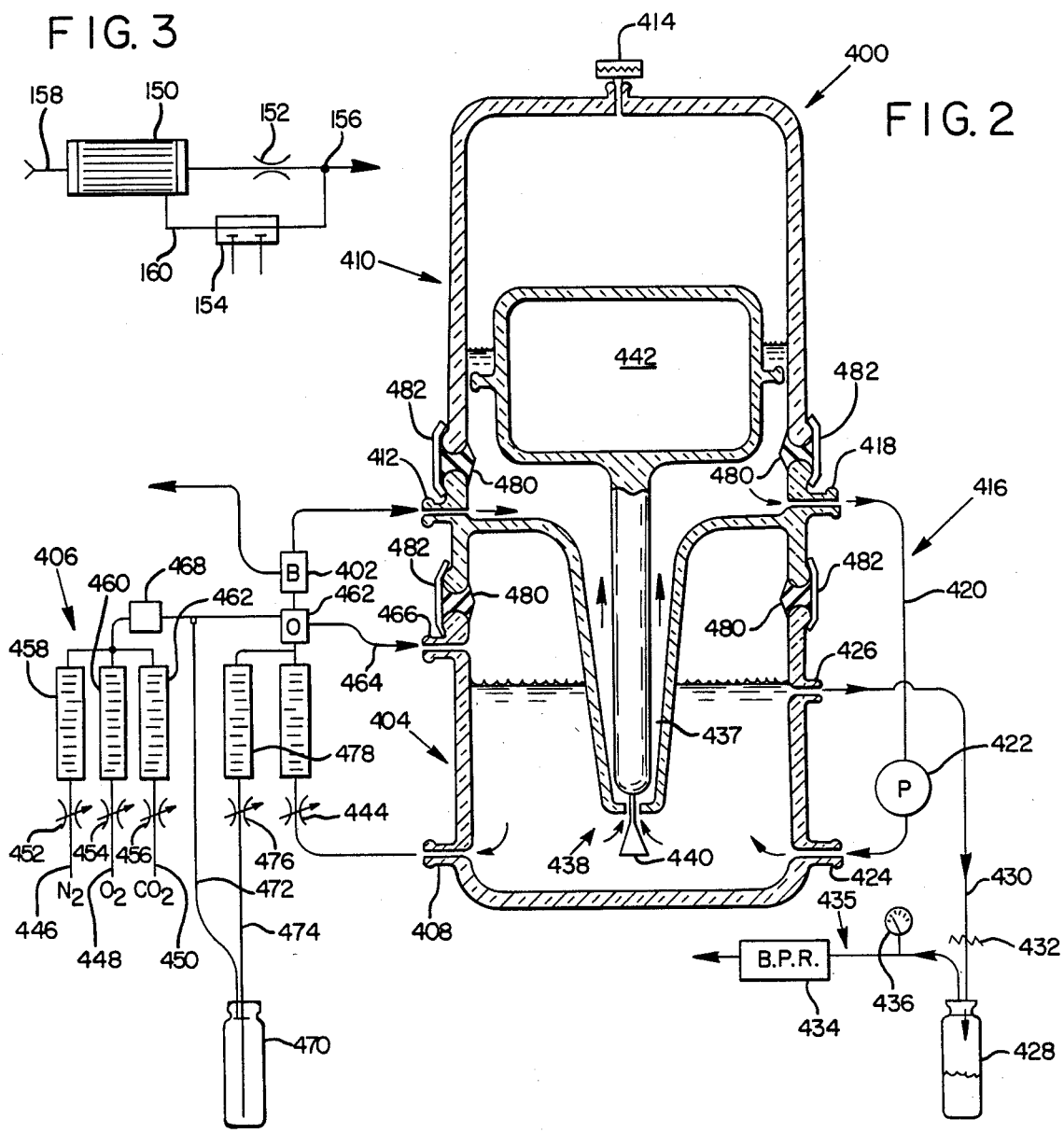
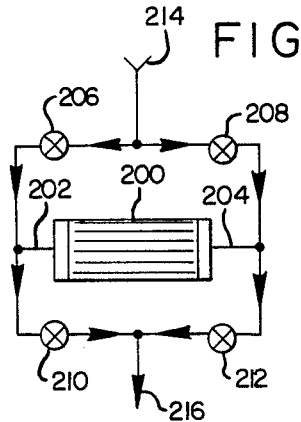
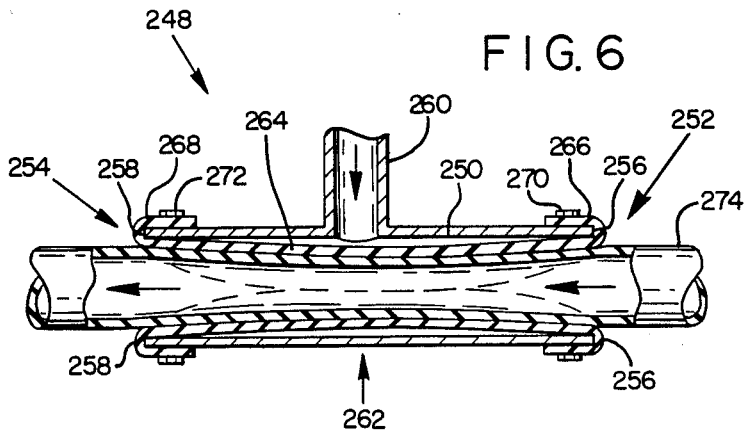

4,889,812

BIOREACTOR APPARATUS

BACKGROUND OF THE INVENTION

This invention relates to bioreactor apparatuses and particularly to the control systems for bioreactor apparatuses that include hollow fiber bioreactors.

Hollow fiber bioreactors are increasingly being used for the synthesis of biological products. The hollow fibers within the bioreactor cartridge serve as a support and a nutrient conduit for cell culture. Cells are typically grown on the outside of the semipermeable fibers and are maintained by perfusion of nutrient medium which is circulated within the fibers. Waste products excreted by the cultured cells perfuse into the fibers and are carried away in the nutrient medium. Desirable cellular by-products, such as monoclonal antibodies, are typically too large to perfuse into the fibers and are thus trapped in the extracapillary region of the bioreactor cartridge.

The task of controlling operation of the bioreaction process is very demanding. In many applications, the desired cell by-products are produced at an extremely slow rate. Sometimes the bioreactor system must operate continuously for weeks or months at a time in order to accummulate a fraction of a gram of useable product. Accordingly, it is crucial that all components in the system be extremely reliable.

The costs associated with many bioreactor experiments, both in terms of financial and opportunity costs, are quite high. The nutrient medium required to sustain the cells over a several month period may cost thousands of dollars. More importantly, the cells being cultured are sometimes exceedingly difficult to obtain. If a bioreactor experiment utilizing such a cell culture is aborted, it may be months before the product can be produced again. Thus, any malfunction in the system can have long term effects on a project.

The most serious problem in bioreactor systems is maintaining absolute sterility in the system throughout the months during which the project may run.

Another concern in bioreactor design is the biocompatibility of the system. The greater the number of materials the biological fluid contacts, the higher the risk of system contamination caused by leeching of trace chemicals into the fluid. Similarly, biocompatibility problems can arise if the design of the system does not facilitate absolute sterilization of the apparatus before use.

In prior art hollow fiber bioreactor systems, nutrient fluid is pumped from a reservoir, through the bioreactor, and returned to the reservoir. The concentration of waste products in the reservoir is moderated by the continuous addition of fresh fluid by a pump linking a bottle of fresh nutrient fluid to the reservoir. The waste product concentration in the reservoir is further moderated by continuously pumping a small amount of nutrient fluid from the reservoir to a waste container. By this technique, the nutrient fluid in the reservoir is always maintained in a relatively fresh state.

Prior art patents illustrating such hollow fiber bioreactor systems include U.S. Pat. Nos. 3,821,087 to Knazek, et al. and 3,883,393 to Knazek, et al., both of which patents are herein incorporated by reference.

Such prior art systems suffer from a number of serious drawbacks. Most important is the risk of contamination associated with the supply of fresh fluid to, and the removal of spent fluid from the sterile reservoir. The reliability f these systems is another concern. The failure of any of the three pumps would abort the experiment with virtually no hope of recovery.

Accordingly, a need remains for an improved bioreactor system.

SUMMARY OF THE INVENTION

It is an object of the present invention to provide a reliable bioreactor system.

It is a further object of the present invention to provide a bioreactor apparatus in which risk of contamination is minimized.

It is a still another object of the present invention to provide an inexpensive bioreactor apparatus.

It is yet a further object of the present invention to provide a more uniform pattern of cellular growth in a hollow fiber bioreactor.

It is yet another object of the present invention to provide a bioreactor system in which a cell culture can be maintained for an extended period of time with high yield.

It is another object of the present invention to provide an improved valve for use in a bioreactor system.

It is still another object of the present invention to provide an improved pump for use in a bioreactor system.

It is yet another object of the present invention to provide a sterile infusion/extraction device for coupling to a bioreactor system.

It is still another object of the present invention to provide a gas-pressure driven bioreactor system.

It is a further object of the present invention to optimize the biocompatibility of the components of a bioreactor apparatus.

The foregoing and additional objects, features and advantages of the present invention will be more readily apparent from the following detailed descriptions of preferred embodiments thereof, which proceed with reference to the accompanying drawings.

BRIEF DESCRIPTION OF THE DRAWINGS

FIG. 1 shows a bioreactor system according to the present invention.

FIG. 2 shows another bioreactor system according to the present invention.

FIG. 3 shows a sterile infusion/extraction device according to the present invention adapted to probe certain physical characteristics of nutrient fluid.

FIG. 4 shows a nutrient fluid flow reversing apparatus according to the present invention.

FIG. 5 shows an alternate nutrient fluid flow reversing apparatus according to the present invention.

FIG. 6 shows a nonintrusive two-way bioreactor valve according to the present invention.

FIG. 7 shows a bioreactor pump according to the present invention.

DETAILED DESCRIPTION

With reference to FIG. 1, one embodiment of a bioreactor 10 according to the present invention includes a fluid reservoir 12, a pump 14 and a bioreactor 16. Nutrient fluid 18 from reservoir 12 is pumped by pump 14 through bioreactor 16 and is returned to reservoir 12.

Bioreactor 16 typically comprises a plurality of semipermeable fibers or capillaries mounted within a cartridge. The nutrient fluid flows through the lumen of the fibers and perfuses to the extracapillary space. The cells to be cultured are typically placed in the extra capillary region and are nourished by the perfusion of nutrient through the semipermeable membrane. The bioreactor 16 included in illustrative apparatus 10 allows transfer of materials having a molecular weight up to 90,000 and includes an extracapillary region surface area of 1.3 square meters. In FIG. 1, the lumen ports which communicate with the opposite ends of the fibers are marked 20 and 22. The extracapillary ports, which communicate with the extracapillary region surrounding the fibers, are marked 24 and 26. It is through these extracapillary ports that the cell culture is typically introduced at the beginning of an experiment and through which harvested cellular by-products are withdrawn.

In more detail, illustrated bioreactor system 10 includes two fluid circuits: a first fluid circuit 28 for the nutrient fluid and a second fluid circuit 30 for the harvest fluid. The first fluid circuit 28 includes nutrient reservoir 12, pump 14, a pressure regulator 32, a flow adjusting device 34 and a flow indicating device 36. Pump 14 typically produces a flow of between twenty-five and one thousand milliliters per minute through first fluid circuit 28. The pressure at the output of pump 14 is held constant by pressure regulating device 32, which typically comprises a ball and spring check valve. The rate of fluid flow through the first fluid circuit is adjusted by flow adjusting device 34, which may comprise a variable orifice. The rate of flow is indicated by flow indicating device 36, which may comprise a rotameter.

In an alternative embodiment, pressure regulator 32 can be omitted and a variable speed pump substituted for the illustrated fixed speed pump 14. In still other embodiments, pump 14 can be operated in a pulsatile mode. Pulsatile flow causes a degree of turbulence in the bioreactor which may assist the transfer of nutrient fluid to the cell culture across the semipermeable membrane. A pulsatile flow also more accurately simulates the in vitro environment from which the cell culture was taken.

First fluid circuit 28 further includes an oxygenator 38. Oxygenator 38 can comprise a membrane device in which the nutrient fluid 18 circulates along one side of a membrane and a controlled mixture of gases passes along the second side. In the illustrated embodiment, oxygenator 38 is supplied with a controlled mixture of gas through a gas inlet 40, a sterile filter 42, a gas flow adjusting device 44 and a gas flow indicating device 46. This gas is fed into a first port 48 on the gaseous side of the membrane. A second port 50 on the gaseous side of the membrane exhausts the gas to the atmosphere through another sterile filter 52.

Continuing along first fluid circuit 28, the nutrient fluid passed through a flow direction control assembly 54, comprised of a plurality of valves 56, 58, 60 and 62. Flow direction control assembly 54 allows the direction of nutrient flow through the bioreactor 16 to be reversed. Flow direction control assembly 54 is discussed in more detail below.

From tubing 64 of first fluid circuit 28, the nutrient fluid flows through the bioreactor, either from lumen port 22 to lumen port 20, or from lumen port 20 to lumen port 22, depending on the configuration of flow direction control valves 56–62. The output flow from the bioreactor is routed to line 66 by the flow direction control assembly 54. Line 66 takes the fluid flow to a sterile infusion/extraction device 68 that allows fresh fluids to be added to the first fluid circuit or nutrient fluids to be withdrawn from the first fluid circuit. The details of this device 68 are discussed more fully below. The output fluid flow from infusion/extraction device 68 is returned to reservoir 12 through line 70. Line 70 introduces the returning nutrient fluid to the reservoir below the fluid level, so as to prevent the proteinaceous material from foaming. Reservoir 12 includes a sterile vent 72 for maintaining the contents of reservoir 12 at atmospheric pressure.

The positive nutrient fluid pressure throughout most of first fluid circuit 28 reduces the risk of contamination and keeps the dissolved gases in solution.

As nutrient fluid 18 circulates through bioreactor 16, the cell culture depletes certain nutrient components from the fluid and adds waste products to it. Accordingly, it is important that the nutrient fluid be refreshed to assure satisfactory cell culture. In the present invention, this can be effected by alternately withdrawing used nutrient fluid from the first circuit and replacing it with fresh nutrient fluid. This is preferably accomplished with the use of a single, reversible pump 74 and a system control unit 76. Reversible pump 74 is in fluid communication with a fresh fluid source and a waste fluid outlet. To withdraw used fluid from first fluid circuit 28, reversible pump 74 is operated in a first direction and a waste fluid outlet valve 78 is opened. Pump 74 extracts used fluid from first fluid circuit 28 through the sterile infusion/extraction device 68 along line 80. This fluid extracted to line 80 is pumped through line 82, through open valve 78, through a sterile filter 84 and to the waste fluid outlet 86. Reversible pump 74 is typically operated in this first direction until a desired amount of used fluid has been withdrawn from first fluid circuit 28. Operation of reversible pump 74 in the first direction then stops and waste fluid outlet valve 78 is returned to its closed position by system control 76.

To add fresh nutrient fluid to first fluid circuit 28, system control 76 causes reversible pump 74 to operate in a second, opposite direction. In this mode, pump 74 draws fresh fluid from a fresh fluid inlet 88 through a sterile filter 90, through a fresh fluid inlet valve 92 (which has been opened by system control 76), through line 82, to line 80 and infused into the first fluid circuit through infusion/extraction device 68. Reversible pump 74 is typically operated in this second mode until a desired amount of fresh fluid has been added to the system.

In typical operation, reversible pump 74 is operated in its first mode to withdraw a quantity of used fluid, and then operated in its second mode to add a corresponding amount of fresh fluid. By this technique, the volume of nutrient fluid 18 in the first fluid circuit 28 is maintained relatively constant and is kept refreshed.

In the preferred embodiment, system control unit 76 includes one or more devices for monitoring the volume of fluid in the first fluid circuit. In the illustrated embodiment, these volume sensing devices include first and second infrared level detecting devices 94 and 96. These devices emit infrared radiation into the fluid nutrient reservoir 12 at first and second levels and determine, based on the amount of radiation reflected, whether or not the nutrient level in the reservoir is above or below these levels. Normally, reservoir 12 is maintained so that the level of fluid nutrient 18 is slightly above the level at which second detector 96 is placed. Periodically, such as once an hour, system control 76 can cause reversible pump 74 to begin operation in its first mode so as to reduce the level of fluid in reservoir 12. System control 76 allows this withdrawal of used fluid to continue until first level detector 94 indicates that the level of nutrient fluid in the reservoir has fallen below the first level. At this point, system control 76 causes reversible pump 74 to switch to its second mode and add fresh fluid to first fluid circuit 28. Operation of reversible pump 74 in this mode is continued until system control 76 determines, through second level detector 96, that the level of fluid in reservoir 12 has returned to its initial, second level. At this point, system control 76 causes reversible pump 74 to return to its idle state for the remainder of the illustrative hour period.

In the above described refresh technique, a single pump serves the purpose of two pumps in the prior art, thereby increasing system reliability. Furthermore, reversible pump 74 operates at a very low duty cycle, further increasing its life.

In other embodiments of the present invention, reversible pump 74 could be replaced by two single direction pumps which would also be operated at a very low duty cycle, substantially increasing their reliability.

It is sometimes desirable to periodically sample the nutrient fluid. In the FIG. 1 embodiment, fluid in the input line of the bioreactor 16 can be sampled through a valve 98 and sterile filter 100 at a bioreactor input sample port 102. A similar arrangement, not shown, could be used to sample fluid in the output circuit of bioreactor 16, such as at line 70. In the illustrated embodiment, however, a different technique is used which allows the proteinaceous materials in the nutrient fluid to be preserved within the first fluid circuit and not expelled with the sample. This is accomplished by a third use of reversible pump 74. Pump 74 is operated in its second mode, extracting fluid from first circuit 28 and routing it through an open sample outlet valve 104, a sterile filter 106 and to a sample outlet 108. The proteinaceous materials in the fluid nutrient are kept in first circuit 28 by infusion/extraction device 68, thereby allowing these costly fluid supplements to remain in the system.

The second fluid circuit 30 illustrated in FIG. 1 can be used to circulate, withdraw or supplement the harvest fluid resident in the extracapillary region of bioreactor 16. All three of these operations are again effected by reversible pump 74. In normal operation, harvest fluid valves 110 and 112 are open and valve 114 is closed. This results in a continuous circulatory path from extracapillary ports 24, through line 116, through pump 74, through line 118, and back into the extracapillary region of the bioreactor via extracapillary port 26. While reversible pump 74 is operating (either to withdraw used fluid from first circuit 28, supply fresh fluid to circuit 28, or sample bioreactor fluid from circuit 28) it simultaneously causes the harvest fluid in second fluid circuit 30 to circulate, either in one direction or the other. This circulation through the extracapillary region of the bioreactor is not constant. It only occurs during the low duty cycle periods of operation of pump 74. However, it has been hypothesized that periodic circulation of the harvest fluid reduces the concentration of cell by-products immediately adjacent the cell walls, thereby enhancing production of cell by-products.

It is at times desirable to supplement the harvest fluid with optimizing growth factors, such as serum. In the illustrated embodiment, system control 76 can cause valve 114 to open, thereby putting a source of optimizing growth factors, coupled to harvest port 120, in fluid communication with the second fluid circuit 30. System control 76 causes reversible pump 74 to operate in its second direction and further causes valve 110 to close, thereby inducing a flow of the optimizing growth factor into the second fluid circuit. When the addition of this material is complete, system control 76 causes valve 110 to return to its open position and valve 114 to return to its closed position.

To withdraw harvest fluid from second circuit 30, system control 76 causes valve 110 to close and valve 114 to open. Pump 74 is operated in the first direction, withdrawing nutrient fluid from extracapillary port 24 and passing it through lines 116, 118, pump 74, through open valve 112 and to the harvest port 120. The reduced pressure in the extracapillary region caused by such operation of pump 74 in its first direction increases the transmembrane pressure in dialyzer 16, causing additional nutrient fluid to perfuse through the membrane to help replace the fluid withdrawn out harvest port 120.

Reversible pump 74 desirably comprises a dual channel reversible peristaltic pump having a diameter of approximately five inches. The tubing 128 of the second fluid circuit that passes through peristaltic pump 74 is quite small, so that if continuously operated, pump 74 would produce a flow in second fluid circuit 30 of approximately fifteen milliliters per minute. The tubing 130 in the peristaltic pump, through which nutrient fluid is infused into or extracted from first fluid circuit 28, is much larger, so that if continuously operated, pump 74 would produce a flow of approximately one hundred milliliters per minute into or out of the first circuit.

The use of a single pump 74 for the six enumerated functions, three in the first fluid circuit and three in the second fluid circuit, greatly simplifies system design, reduces system cost and increases system reliability. Since the rate at which these fluid transfers are made is not critical, an inexpensive one-speed, AC operated peristaltic pump can be used, further decreasing costs over prior art systems which use variable speed, DC pump technology.

Desirably, system control 76 is an electronic control unit. Alternatively, all elements monitored and controlled by system control 76 can be monitored and controlled manually. In the illustrated embodiment, system control device 76 includes a warning circuit to alert the operator of possible system malfunctions. For example, system control device 76 can be programmed to remember the expected length of time needed for pump 74 to remove a volume of fluid from the first fluid circuit 28 corresponding to the difference in fluid levels between the first level sensor 94 and the second level sensor 96. If first sensor 94 does not indicate that the fluid in the reservoir has fallen beneath the first level in the expected period of time, a warning signal can be sounded to alert the operator to a possible malfunction in the circuitry associated with the removal of used fluid.

Similarly, system control device 76 can be programmed to remember the expected length of time needed for pump 74 to infuse a replacement volume of fresh nutrient liquid into the system corresponding to the difference in volumes between the first and second levels in the nutrient reservoir. If the second level detector 96 does not indicate that the first fluid circuit has been refilled to this level within an expected time period, another warning can be sounded to indicate a potential malfunction in the fluid refresh circuitry.

If system control device 76 is a microprocessor based circuit, a multitude of other system functions can be added. For example, the circuit can be programmed to monitor and regulate the pH of the nutrient fluid by the controlled addition of a compensating factor. Similarly, the gas concentration in the fluid can be monitored and regulated by the control device. The microprocessor can also be used to automate harvesting of the cell by-products, as by withdrawing a predetermined volume of harvest fluid from the bioreactor 16 periodically according to a predetermined schedule. In such application, harvest port 120 of FIG. 1 can be extended to a refrigerated sterile collection container. A sterile connection made to such container at the beginning of the cell culture process would eliminate the risk of subsequent system contamination by the later connection or disconnection of a container to the harvest port 120. In the preferred embodiment of the present invention, a microprocessor is employed to automate all aspects of cell culture, so that the system requires human intervention only in the event of a component failure.

For optimum cell culture, it is important that the temperature of the fluid nutrient be carefully regulated. In the illustrated embodiment, this is effected by a temperature control device 122 which monitors the temperature of nutrient fluid in reservoir 12 by a thermocouple 124 and regulates the heat provided to the system by electric heater 126 accordingly. In other embodiments, heater 126 may comprise an external water bath, or the entire system can be operated in a controlled environment, such as an incubator.

In the preferred embodiment of the present invention, reservoir 12, pump 14, flow adjusting device 34 and flow indicating device 36 are all autoclavable. The system elements above junctures 132 (with the exception of the roller mechanism of peristaltic pump 74, flow direction control circuitry 53, system control 76 and temperature control 122) are typically disposable parts made of inert materials which are purchased in a sterilized condition and discarded after an experiment has been run, thereby enhancing system sterility and biocompatibility.

Although the above discussion has assumed, for purposes of illustration, that the cell culture is growing in the extracapillary region of bioreactor 16 and is nourished by nutrient fluid circulating through the fibers, these positions may be reversed. That is, the cells may be cultured in the inside of the fibers and the nutrient fluid circulated in the extracapillary region. Similarly, although bioreactor 16 is illustrated as having only two extracapillary ports, in other embodiments it may be desirable to use a bioreactor cartridge having more or less extracapillary ports. The addition of other extracapillary ports would facilitate the addition of other system features. For example, it may be desirable to circulate the harvest fluid using two ports and to extract it using a third port. This third port could be connected to a recovery system that isolated and purified the desired biological by-product from the harvest fluid. Such additional ports could also be used to supplement the harvest fluid with serum at the same time as it is being circulated in the second fluid circuit.

In still other embodiments of the invention, it may be desirable to provide a plurality of hollow fiber bioreactor cartridges operated from the bioreactor system 10 of FIG. 1. Such bioreactor cartridges may be connected in series or parallel, as best fits the particular application involved.

While the preferred embodiment has been illustrated with reference to a continuous circulation system, the principals embodied therein are equally applicable to a semi-batch process. In such process, a large reservoir of nutrient fluid is circulated through the bioreactor and collected in a waste container; not recirculated. Accordingly, the word circulate in the detailed description is not meant to imply a closed loop, but merely to denote the flow of liquid.

It is, of course, desirable that a bioreactor apparatus design be versatile so that it can be adapted to the production of a broad range of biological products. The hollow fiber bioreactor cartridge is a component that lends itself to the production of a broad range of products. However, it should be recognized that the present invention has applicability to a broad range of other bioreactor designs that do not include hollow fiber bioreactor cartridges.

Infusion/Extraction Device

The sterile infusion/extracting device 68 illustrated in FIG. 1 is discussed in detail below. In many biological systems, it is desirable to provide a sterile tap into a flow of sterile fluid. This may be desirable, for example, to introduce additional sterile fluid into a flow of sterile fluid, or to withdraw a portion of a sterile fluid flow. In the present invention, device 68 comprises a membrane device having first and second chambers separated by a membrane. The first chamber is in fluid communication with first and second circulatory ports. The second chamber is in fluid communication with at least one coupling port. In operation, the sterile fluid is routed through the first chamber, through the first and second circulatory ports. Sterile communication with this flow is effected by producing a pressure gradient across the membrane, so as to produce an infusion of fluid into, or an extraction of fluid out of the flow passing through the first chamber. In the illustrated bioreactor, this device comprises a hollow fiber bioreactor. The sterile flow of fluid is passed through the lumen of the fibers. The material to be infused is applied to the extracapillary region through an extracapillary port. Similarly, the material extracted is also withdrawn from the extracapillary region through the extracapillary port.

By varying the pressure gradient across the membrane, the rate of mass transfer between the two interfacing systems can be regulated. In the illustrated embodiment, a hollow fiber bioreactor having a pore size of 0.2 microns and a surface of area of 1.3 square meters is used. As used in FIG. 1, infusion/extraction device 68 refreshes the nutrient fluid without loss of sterilization in the first fluid circuit.

In other applications, the infusion/extraction device can be used to divert spent nutrient fluid to another process or recycling system.

In still other applications, the infusion/extraction device can be provided with a plurality of extracapillary ports to implement other system functions. For example, a multiport infusion/extraction device can provide an interface to back-up components which are activated in the event of a system component failure. In FIG. 1, if reversible pump 74 were to fail during an experiment, the experiment may have to be aborted. If infusion/extraction device 68 is provided with a second extracapillary port, a redundant reversible pump (not shown), and associated valving can be interfaced to the system. System control 76 can be provided with means to detect a system failure and switch the appropriate valves to allow the redundant pump to take over operation of the failed pump's 74 function. In other applications, a multi-extracapillary port infusion/extraction device can be used to couple a plurality of fluid supplement sources to the system at the beginning of an experiment. As a certain supplement is needed in the nutrient, it can be controllably added through the infusion/extraction device. Such supplementation technique minimizes the breach-of-sterility risk inherent in the attachment of any device to the system after the experiment has begun.

FIG. 3 shows a novel application of the infusion/extraction device of the present invention to probe the nutrient fluid for certain physical characteristics, such as pH, oxygen and glucose. The nutrient fluid usually includes proteinaceous components. If these components are allowed to come into contact with instrumentation probes, the operation of the probes can be degrated. Accordingly, the infusion/extraction device of the present invention is adapted to produce a flow of filtered nutrient fluid free from these proteinaceous components. As illustrated in FIG. 3, this apparatus includes an infusion/extraction device 150, a flow restricting device 152 and a probe manifold 154. Flow restricting device 152 produces a pressure gradient across its input and output ports. Flow restriction device 152 also produces a corresponding pressure gradient across the membrane of the infusion/extraction device. The pressure at outlet 156 of flow restricting device 152 is lower than the pressure at a point 158 at the input of the infusion/extraction device. This pressure gradient produces a flow of fluid through the membrane and into line 160, which passes through probe manifold 154. This filtered fluid can be monitored for a variety of physical characteristics. After monitoring, the filtered fluid flow is returned to the main fluid flow at point 156, thereby reestablishing the proteinaceous concentration of the sterile fluid present at input 158. By this technique, the probes and the probe manifold 154 are protected against protein deposition, yet are able to monitor the pH, oxygen, glucose, etc. of the nutrient fluid flow. The illustrated apparatus produces this flow of nonproteinaceous fluid without the addition of another pump to the bioreactor system.

Flow restricting device 152 is typically an orifice. The pressure drop across this orifice is not critical. The transmembrane pressure need only be sufficient to produce a flow of sterile fluid adequate to obtain an accurate response from the probes. If the filtered sterile fluid flow is too slow, the measurements obtained from the probes may not reflect actual real time conditions.

In the preferred embodiment, the apparatus of FIG. 3 is a three port device of unitary construction which includes the infusion/extraction device, the flow restricting orifice and the probe manifold.

Although a hollow fiber bioreactor cartridge is included in the preferred embodiments of the infusion/extraction device, other devices, such as plate and frame membrane devices, can also be used.

Nutrient Flow Direction Control

In prior art bioreactor systems, such as are discussed in U.S. Pat. Nos. 3,821,087 and 3,883,393, the direction of nutrient fluid flow through the hollow fiber bioreactor is constant. The fluid always enters at a first end and exits at a second end. Thus, the cells growing at the first end receive a relatively fresher nutrient fluid than cells growing near the second end. Over long periods of time, this unequal nutrient distribution can produce an asymmetrical cellular distribution, with a denser cell mass near the first end than near the second. This uneven distribution of cells along the hollow fibers makes inefficient use of the limited extracapillary region, thereby reducing total product yield. Furthermore, in regions in which the cell mass is unnecessarily dense, growth inhibitors produced by the cells can diminish cell productivity.

To overcome these disadvantages, the present invention includes a system for changing the direction of fluid flow through the bioreactor cartridge periodically. Changing the direction of fluid flow aids in the diffusion of the nutrients required for cell growth and in the diffusion of growth inhibiting substances away from the cells. In the preferred embodiment of the flow reversing apparatus of the present invention, shown in FIG. 4, a hollow fiber bioreactor cartridge 200, having a first circulatory port 202 and a second circulatory port 204, is connected to an arrangement of four valves: 206, 208, 210 and 212. The valves 56, 58, 60 and 62 in FIG. 1 correspond to the valves 206, 208, 212 and 210 in FIG. 6, respectively. In a first state, first and third valves 206 and 212 are open and the other valves are closed, causing nutrient fluid applied to apparatus input 214 to flow through bioreactor 200 from first port 202 to second port 204. The flow passes through open two-way valves 206 and 212 and exits the apparatus at output 216.

In a second state, second and third valves 208 and 210 are open and the other valves are closed, causing nutrient fluid to flow through bioreactor 200 from port 204 to port 202.

The means for alternating the apparatus between its first and second flow direction states can comprise a timer circuit which alternates the apparatus between its two states for fixed periods of time. Alternatively, the valves can be switched manually between their two states.

For biocompatibility reasons, discussed below, the use of special two-way valves in the flow direction control apparatus is preferred. In another embodiment, shown in FIG. 5, a single four-way valve 220 can be used. In its first state, valve 220 causes fluid provided to input 222 to flow through hollow fiber bioreactor 224 from a first circulatory port 226 to a second circulatory port 228. From the second circulatory port 228 the fluid is routed, again through four-way valve 220, to the apparatus fluid output 230.

In the second state, valve 220 is switched so that fluid introduced at apparatus input 222 is routed through bioreactor 24 from second circulatory port 228 to first circulatory port 226. From first circulatory port 226 the fluid is routed, again through four-way valve 220, to the apparatus output 230.

Embodiments such as that shown in FIG. 5, which use a four-way valve, and other embodiments, not shown, which use two three-way valves, are disadvantageous because of the additional expense associated with these more complex valves. More importantly, however, is the intrusive nature of such valves in the delicate bioreactor environment. It is important, when dealing with biological liquids, that all materials coming in contact with the liquid be inert. Three-way and four-way valves are typically machined from metal. Various contaminants may appear in the metal, or may have been used in the processing of the valve, which may interfere with a biological experiment. Similarly, the complex machined shape of conventional valves includes cavities and corners into which the chemical sterilization agents may not penetrate, increasing the likelihood of a contaminant surviving the sterilization process. Accordingly, a smooth bore nonintrusive valve of inert material is highly desirable for this and other applications in bioreactor systems. Such a valve is discussed below.

Nonintrusive Two-Way Bioreactor Valve

A nonintrusive two-way valve 248 suitable for use with the present invention is shown in FIG. 6. The valve includes an elongated rigid tubular housing 250 having a first open end 252 and a second end open end 254. First and second open ends 252, 254 are defined by circular peripheral edges 256 and 258. The elongated rigid housing further includes a control port 260 which intersects the circular housing near its midsection 262.

Coaxially disposed within elongated rigid housing 250 is an elongated deformable sleeve member 264. Sleeve member 264 has first and second ends 266, 268 which are united to the peripheral edges 256, 258, respectively of the first and second open ends of the housing. As shown in FIG. 6, the deformable sleeve members can be turned back over the outside of the elongated rigid housing at ends 266, 268 and fastened to said ends by constricting bands 270, 272, respectively.

Within deformable sleeve member 264 is routed a piece of deformable tubing 274 used in the bioreactor which carries a fluid flow to be controlled. Tubing 274 is typically made of silicone rubber or other inert material.

To close valve 248, a pressure is applied to the control ports 260. This pressure, whether produced by the application of gas or liquid, causes the deformable sleeve member 264 to constrict. This, in turn, causes the deformable bioreactor tubing 274, routed through the sleeve member 264, also to constrict, thereby occluding flow of sterile fluid through this tubing.

Alternatively, the fluid flow through valve 248 can be occluded by applying a vacuum to control port 260, rather than an increased pressure.

By this technique, a valve can be provided in a bioreactor apparatus without the drawbacks associated with conventional valves. The biological liquid does not come in contact with any foreign material. Instead, it contacts only the inert sterile tubing regularly used in bioreactor applications. This tubing has a smooth bore, thereby minimizing the risk of a hardy contaminant surviving the chemical sterilization process, as sometimes occurs in conventional valves. No connections to or from the valve are required, thereby reducing the chance of failure and greatly reducing the risk of contamination.

The illustrated valve provides several advantages over pinch clamps used in certain application in the prior art. Pinch clamps abrade the tubing, as they act on a relatively confined area of its length. Furthermore, they have a very limited life. In the flow reversing circuit described above, the valves may be switched every minute for a period of several months. A pinch valve would quickly abrade the tubing and risk its rupture. The present invention, by contrast, provides a gentle milking of one deformable tube on another. This allows the bioreactor tube being constricted to remain patent for a much longer period of time.

Even if components of valve 248 were to fail, as for example if rigid housing 250 or deformable sleeve 264 were to rupture, the sterility of the fluid would be preserved and contamination avoided.

Bioreactor Pump

Before a bioreactor experiment can be started, all system components must be sterilized. This is typically done in a high temperature autoclave. Autoclavable pumps can be expensive. To lower the cost of a bioreactor system, it is desirable to develop inexpensive pumping components that can be provided in sterile packages, installed in a sterile system, used, and then discarded. The pump 300 illustrated in FIG. 7 is a preferred form of such a pump and can be used for pump 14 in FIG. 1.

Pump 300 of FIG. 7 includes two principal components: a sterile pumping assembly 302 and an actuator assembly 304. Sterile pumping assembly 302 pumps sterile fluid from an inlet 306 to an outlet 308. The motive energy for driving pumping assembly 302 is provided by actuator assembly 304. In the preferred embodiment, actuator assembly 304 magnetically drives a pumping membrane 310 of the pumping assembly by exerting a magnetic force on fixed magnet 312 which is attached to membrane 310. Magnet 312 can be attached to membrane 310 by a rubber rivet 313 ultrasonically bonded to membrane 310. When actuator 304 attracts magnet 312, membrane 310 moves down to the illustrated position. This movement reduces the pressure in region 314, thereby causing flap 316 of umbrella valve 317 to move downwardly and admit fluid from inlet 306 to region 314. When, on the opposite stroke, actuator 304 repels magnet 312, membrane 310 is moved upwardly until it abuts the base 319 of a duckbill valve 318, thereby driving fluid from region 314 through duckbill valve 318 and to the fluid outlet 308.

In the preferred embodiment, actuator 304 comprises an electromagnet driven by a DC signal of alternating polarity. The frequency at which the polarity alternates is varied to vary the pumping rate. When used as pump 14 in the bioreactor apparatus 10 of FIG. 1, the pump of FIG. 7 is operated to pump approximately one hundred milliliters of fluid per minute from inlet port 306 to outlet port 308.

In alternative embodiments, actuator 304 may be an electromagnet driven by a conventional AC signal.

In still other embodiments, actuator 304 may comprise a solenoid or other electromechanical linkage which drives membrane 310.

Pump 300 is constructed so that pumping assembly 302 can readily be separated from the actuator assembly. In the bioreactor apparatus of FIG. 1, the pump is inverted from the position illustrated. The pumping assembly 302 is mounted on top of reservoir 12 and mates with a tube that extends down into the nutrient fluid which protrudes from a molded plug sealing the reservoir. Actuator assembly 304 is positioned in pumping assembly 302 and maintained in place by a releasable bracket. After the experiment or production run is completed, the inexpensive plastic and rubber pumping assembly 302 can be removed and discarded and later be replaced with a new, sterile unit for use in the next process.

Gas Driven Bioreactor

In the bioreactor apparatus 10 of FIG. 1, reliability is increased by eliminating one of the three pumps typically used in prior art hollow fiber bioreactor apparatuses. In the embodiment described below, pressurized gas provides a motive force for moving the fluid nutrient through the bioreactor cartridge, so that a continuous flow bioreactor apparatus can be constructed with a single pump.

With reference to FIG. 2, the gas driven bioreactor apparatus 400 of the preset invention includes a hollow fiber bioreactor 402, a nutrient fluid reservoir 404 and a source of pressurized gas 406. The pressurized gas pressurizes reservoir 404, forcing fluid to pass from an outlet 408 of the reservoir 404 through the bioreactor 402 and into a second reservoir 410 through an inlet 412. Second reservoir 410 is maintained at a pressure less than first reservoir 404. In the preferred embodiment, second reservoir 410 is maintained at atmospheric pressure through a sterile vent 414.

Bioreactor apparatus 400 further includes a fluid circuit 416 for returning nutrient fluid from second reservoir 410 to first reservoir 404. Return circuit 416 includes an outlet 418 in second reservoir 410, a line 420, a pump 422 and an inlet 424 into the first reservoir 404. Pump 422 operates to replenish reservoir 404 from reservoir 410.

Bioreactor 400 further includes a second circuit 437, apart from circuit 416, by which reservoir 404 and reservoir 410 are maintained in fluid communication. Second circuit 437 allows the controlled transfer of nutrient fluid from first reservoir 404 to second reservoir 410 so as to maintain a substantially constant volume of nutrient fluid in second reservoir 410. Circuit 437 desirably includes a variable size orifice 438 through which fluid passes from the first reservoir 404 to the second reservoir 410. This orifice is occluded by an occluding member 440 whose position is determined by the level of fluid in the second reservoir 410. Occluding member 440 is connected to a float 442 which floats in the nutrient fluid in reservoir 410. If the level of nutrient fluid in reservoir 410 drops, the restriction of orifice 438 by occluding member 440 decreases, allowing increased fluid to flow from the pressurized reservoir 404 to the reduced pressure reservoir 410. Similarly, if the level of fluid in second reservoir 410 increases, occluding member 440 tends to reduce the size of orifice 438, thereby reducing the transfer of fluid from the pressurized reservoir 404 to the reduced pressure reservoir 410. By this system, automatic regulation of the volume of fluid in second reservoir 410 is provided.

In typical operation, the volume of nutrient fluid flow through bioreactor 402 may be five hundred milliliters per minute. This rate can be set by a flow adjusting device, such as a variable size orifice 444. For such operation to continue, pump 422 must supply to first reservoir 404 a volume of fluid equal to at least five hundred milliliters per minute. If this minimum volume of fluid is not provided, the liquid in reservoir 404 will soon be exhausted and circulation will stop.

Desirably, pump 422 provides fluid to reservoir 404 at a rate greater than it is expelled through bioreactor 402. For example, pump 422 may provide seven hundred milliliters per minute to reservoir 404, while only five hundred milliliters per minute are being removed to bioreactor 402. In such case, the seven hundred milliliter per minute flow out of second reservoir 410 through second reservoir outlet 418 exceeds the five hundred milliliter per minute flow into second reservoir 410 from bioreactor 402. In such case, the level of fluid in reservoir 410 will tend to drop, lowering float 442 and opening the variable size orifice 438. This opening will increase the fluid flow from the first reservoir 404 into the second reservoir 410, so that the level of fluid in the second reservoir is maintained. Thus, it can be appreciated that the rate at which pump 422 transfers fluid from the second reservoir to the first reservoir is not critical, provided that it at least exceeds the rate at which fluid is circulated through the bioreactor 402. Any excess over this rate is returned to the second reservoir 410 through the variable size orifice 438.

It should be recognized that illustrated pump 422 only supplies the energy needed to overcome the pressurization in first reservoir 404, so that the fluid therein can be replenished. It does not operate to drive nutrient fluid through bioreactor 402.

The gas pressure that drives the fluid nutrient from first reservoir 404 through bioreactor 402 is provided by pressurized gas bottles connected to gas inlets 446, 448 and 450. The relative proportions of these gases provided to the system is regulated by flow adjusting devices 452, 454 and 456. The rate of each gaseous flow is indicated by indicators 458, 460 and 462. In the illustrated embodiment, the gases applied to the system include nitrogen, oxygen and carbon dioxide. These gases oxygenate the nutrient fluid through an oxygenator 462. As discussed above, oxygenator 462 can comprise a semipermeable device in which the gas is circulated along one side of the membrane and the liquid circulated along the other. The gas exiting the oxygenator on line 464 is provided to a gas input port 466 of the first reservoir. A sterile filter 468 is used in the gas line to maintain system sterility.

The pressurized gas fed through oxygenator 462 and fed to first reservoir 404 is also used to drive fresh nutrient fluid into the first reservoir. A container of fresh nutrient fluid 470 is pressurized through a gas line 472. The pressure applied to fresh fluid reservoir 470 by gas line 472 forces a flow of fluid up line 474, through a flow adjusting device 476 and a flow indicating device 478 and into the nutrient fluid flow through the bioreactor. In the illustrated system, the addition of fresh nutrient fluid to the system is done at a constant, slow rate, such as five milliliters per minute. This rate is adjusted by flow adjusting device 476. As fresh fluid is added to the system from fresh fluid reservoir 470, the total fluid volume in the system tends to increase. The level of fluid in the second reservoir 410 is regulated by the variable orifice device 438, as described above. Accordingly, any excess fluid in the system accummulates in first reservoir 404. As excess fluid is added to this reservoir, a corresponding amount of nutrient fluid is drained out an overflow port 426 to a collection container 428. By this technique, fresh nutrient fluid is added to the system and used nutrient fluid is removed from the system, without any mechanical pumps. Gas pressure provides the sole motive force.

Overflow port 426 is in fluid communication with collection container 428 through a line 430 and a sterile filter 432. Any excess fluid or gas in reservoir 404 is drained through outlet 426 to the container 428. A back pressure regulator 434 is included in an output circuit 435 from the collection container 428 and serves to regulate the pressure in the first reservoir 404. The pressure in this reservoir is indicated by a pressure indicating device 436.

In the illustrated embodiment, reservoirs 404 and 410 are made of Pyrex glass. The couplings 480 are made of Teflon. The components of the unit are held together by stainless steel bands 482.

In typical operation, the pressure in first reservoir 404 is set, by back pressure regulator 434, to be approximately three to ten pounds per square inch above atmospheric pressure. Higher reservoir pressures may be desirable in other applications to induce higher flow rates, especially in those applications in which a plurality of bioreactors are operated simultaneously, in parallel configuration.

The nutrient fluid flow reversing apparatus described above can be used advantageously in bioreactor apparatus 400 to alternate the direction of nutrient fluid flowing through bioreactor 402. Similarly, other features discussed with reference to the bioreactor apparatus shown in FIG. 1 can equally well be applied to the bioreactor 400 in FIG. 2. For example, circulation of the harvest fluid in the extracapillary region of the hollow fiber bioreactor, or the sampling or probing of the nutrient fluid.

Although the illustrated embodiment is designed to operate with just a few liters of fluid, it could readily be scaled up to operate with a much greater fluid volume for full scale production of biological materials.

It is not essential to operation of bioreactor 400 that the pressurized reservoir be physically positioned below the unpressurized reservoir. In other arrangements, the atmospheric pressure reservoir could be below the pressurized reservoir. A float in the atmospheric reservoir could extend upwardly from the fluid and occlude an orifice in the base of the pressurized reservoir. In still another embodiment, the atmospheric pressure reservoir could be beneath the pressurized reservoir and the float could operate to regulate an orifice in the bottom of the atmospheric pressure reservoir. This orifice could then be maintained in fluid communication with the fluid in the upper, pressurized reservoir through a circuit that included a pump.

In prior art oxygenated systems, the energy stored in the pressurized gas is wasted. After it oxygenates the fluid, is vented to the atmosphere. In the present invention, by contrast, this stored energy is harnessed and used to drive the nutrient fluid through the system. This use of pressurized gas also optimizes the biocompatibility of the apparatus by eliminating fluid contact with foreign materials which may be chemically tainted or which may harbor a biological contaminant.

Having described and illustrated the principles of our invention in several embodiments, it should be apparent to those skilled in the art that the invention can be modified in arrangement and detail without departing from such principles. We claim all modifications coming within the scope and spirit of the following claims.

We claim:

1. A bioreactor system comprising:
    bioreactor means having a shell portion and a tube portion for culturing biological materials;
    first circuit means including the tube portion of the bioreactor means for permitting continuous flow of a nutrient fluid through the bioreactor means along a first bioreactor path that defines a loop through the tube portion of the bioreactor means, whereby nutrient fluid is removed from the tube portion and reintroduced thereto, for nourishing the biological materials;
    second circuit means including the shell portion of the bioreactor means for permitting flow of a harvest fluid through the bioreactor means along a second bioreactor path that defines a loop through the shell portion of the bioreactor means, whereby harvest fluid is removed from the shell portion and reintroduced thereto; and
    reversible pump means (a) for adding fresh nutrient fluid to the first circuit means when operated in a first direction, (b) for withdrawing fluid from the first circuit means when operated in a second direction, and (c) for circulating harvest fluid through the second circuit means when operated in either direction.

2. The bioreactor system of claim 1 which further includes:
    pump means for effecting continuous flow of nutrient fluid through the first circuit means; and
    flow adjusting means for adjusting the rate of nutrient fluid flow through the first circuit means.

3. The bioreactor system of claim 1 which further comprises means for reversing the direction of nutrient fluid flow through the bioreactor means along the first bioreactor path.

4. The bioreactor system of claim 1 which further includes:
    reservoir means for containing a reserve of nutrient fluid in the first circuit means;
    first level sensing means for indicating when the level of nutrient fluid in the reservoir means falls below a first level;
    second level sensing means for indicating when the level of nutrient fluid in the reservoir means exceeds a second, higher level;
    control means for causing the reversible pump means to start adding fresh nutrient fluid to the first circuit means when the first level sensing means indicates that the level of fluid in the reservoir means falls below the first level, said control means causing the reversible pump means to stop adding fresh nutrient fluid to the first circuit means when the second level sensing means indicates that the level of fluid in the reservoir means exceeds the second level.

5. The bioreactor system of claim 4 in which the control means periodically causes the reversible pump means to withdraw nutrient fluid from the first circuit means until the first level sensing means indicates that the level of fluid in the reservoir means is below the first level.

6. A bioreactor system having a fresh fluid inlet and a waste fluid outlet, comprising:
    nutrient fluid reservoir means;
    bioreactor means for culturing biological materials;
    pump means for causing nutrient fluid to flow from the reservoir means through the bioreactor means;
    reversible pump means selectively operable in two modes, in the first mode the reversible pump means operating to withdraw nutrient fluid from the reservoir means to the waste fluid outlet and in the second mode operating to add nutrient fluid to the reservoir means from the fresh fluid inlet;
    volume sensing means for indicating when the volume of fluid in the reservoir means is less than a first volume or greater than a second, larger volume;
    means for periodically activating the reversible pump means in its first mode;
    means operable to deactivate the reversible pump means from its first mode when the volume sensing means indicates that the volume of fluid in the reservoir means is less than the first volume;

means for activating the reversible pump means in its second mode when the volume sensing means indicates that the volume of fluid in the reservoir means is less than the first volume;

means operable to deactivate the reversible pump means from its second mode when the volume sensing means indicates that the volume of fluid in the reservoir is greater than the second volume; and control means for monitoring the withdrawal of fluid from the reservoir and the addition of fluid to the reservoir, said means including means for storing first and second signals representing the time period required for the fluid level in the reservoir to fall from the second level to the first level during fluid withdrawal, and the time period required to the fluid level in the reservoir to rise from the first level to the second level during fluid addition, said control means further including alarm means to indicate whenever one of the aforesaid operations is not completed within the required time period.

7. A bioreactor system comprising:

bioreactor means for culturing biological materials;

nutrient fluid circulatory means for circulating nutrient fluid through said bioreactor means along a first path;

harvest fluid circulatory means for circulating harvest fluid through said bioreactor means along a second path; and reversible pump means for controllably adding nutrient fluid to, or removing nutrient fluid from the nutrient fluid circulatory means; said reversible pump means and the harvest fluid circulatory means comprising a dual channel reversible peristaltic pump.

8. An apparatus for circulating fluid nutrient from a fluid nutrient source through a shell and tube type bioreactor having first and second circulatory ports that communicate with first and second ends of the bioreactor lumen tubes, comprising:

first circulatory means for controllably recirculating the fluid nutrient in a loop from the nutrient source, into the bioreactor first circulatory port, out of the bioreactor second circulatory port, and back into the nutrient source;

second circulatory means for controllably recirculating the fluid nutrient in a loop from the nutrient source, into the bioreactor second circulatory port, out of the bioreactor first circulatory port, and back into the nutrient source; and control means for autonomously and periodically alternating the apparatus between first and second states at fixed time intervals, in the first state the first circulatory means being enabled and the second circulatory means being disabled, and in the second state the first circulatory means being disabled and the second circulatory means being enabled, so that the direction of fluid nutrient flowing through the bioreactor alternates.

9. The apparatus of claim 8 in which the first and second circulatory means comprise a four-way valve.

10. The apparatus of claim 8 which further includes:

a fluid nutrient output port;

first, second, third, and fourth valve means for controlling fluid flow, each having an input port and an output port;

means for connecting the fluid nutrient source to the input ports of the first and second valve means;

means for connecting the fluid nutrient output port to the output ports of the third and fourth valve means;

means for connecting the output port of the first valve means and the input valve of the third valve means to the first bioreactor circulatory port;

means for connecting the output port of the second valve means and the input port of the fourth valve means to the second bioreactor circulatory port; and means for switching the valve means between first and second states, in the first state the first and fourth valve means being substantially open and the second and third valve means being substantially closed, and in the second state the first and fourth valve means being substantially closed and the second and third valve means being substantially open.

* * * * *